United States Patent [19]

Grollier et al.

[11] Patent Number: 5,234,635
[45] Date of Patent: Aug. 10, 1993

[54] PROCESS FOR THE PREPARATION OF AN AQUEOUS DISPERSION OF LIPID VESICLES

[75] Inventors: Jean-Francois Grollier, Paris; Georges Rosenbaum, Asnieres; Isabelle Richoux; Francisco Chiodi, both of Paris; Jacky Burin, Sevran, all of France

[73] Assignee: L'Oreal, Paris, France

[21] Appl. No.: 595,473

[22] Filed: Oct. 11, 1990

[30] Foreign Application Priority Data

Oct. 12, 1989 [FR] France ............................... 89 13358
Sep. 26, 1990 [EP] European Pat. Off. ....... 90 402648.1

[51] Int. Cl.$^5$ ..................... B01J 13/12; B01J 13/00; A61K 9/27
[52] U.S. Cl. .................... 264/4.6; 252/314; 424/450
[58] Field of Search .................. 264/4.1, 4.6; 424/450; 252/314

[56] References Cited

U.S. PATENT DOCUMENTS

| | | | |
|---|---|---|---|
| 4,608,211 | 8/1986 | Handjani et al. | 264/4.6 |
| 4,687,661 | 8/1987 | Kikuchi et al. | |
| 4,752,425 | 6/1988 | Martin et al. | 264/4.6 |
| 4,830,857 | 5/1989 | Handjani et al. | 264/4.6 X |
| 4,844,904 | 7/1989 | Hamaguchi et al. | 424/450 |
| 5,000,887 | 3/1991 | Tenzel et al. | 264/4.6 |
| 5,021,200 | 6/1991 | Vanlerberghe et al. | 264/4.1 |
| 5,173,219 | 12/1992 | Kim | 264/4.6 |

FOREIGN PATENT DOCUMENTS

| | | | |
|---|---|---|---|
| 055576 | 7/1982 | European Pat. Off. | 264/4.6 |
| 229561 | 7/1987 | European Pat. Off. | |
| 2619309 | 2/1989 | France | |
| 8807362 | 10/1988 | PCT Int'l Appl. | |
| 11780 | 10/1990 | PCT Int'l Appl. | 264/4.6 |
| 2189457 | 10/1987 | United Kingdom | |

OTHER PUBLICATIONS

French Search Report of FR 89 13358.
Papahadjopoulos et al., *Biochim. Biophys. Acta*, vol. 135 (1967) pp. 639-652.
Chowhan et al., *Biochim. Biophys. Acta*, vol. 266 (1972) pp. 320-342.
Kim et al., *Biochim. Biophys. Acta*, vol. 728, pp. 339-348 (1983).

Primary Examiner—Robert L. Stoll
Assistant Examiner—John M. Covert
Attorney, Agent, or Firm—Cushman, Darby & Cushman

[57] ABSTRACT

To prepare an aqueous dispersion of lamellar lipid vesicles, at least one lipid is dissolved in at least one water-immiscible organic solvent; the organic phase thus obtained is added to an aqueous phase in such amounts that a dispersion of the oil-in-water type is obtained by vigorous stirring; the evaporation of the solvent(s) is carried out with vigorous stirring, the continuous phase of the dispersion always remaining the aqueous phase; and, should it become necessary, the dispersion is concentrated. The process can be carried out at low temperature (of the order of 35° to 55° C.), which makes it possible to encapsulate in the aqueous phase or to introduce into the vesicle sheets heat-sensitive active substances; the lipid concentration in the organic phase can reach up to 50% by weight.

13 Claims, 1 Drawing Sheet

PROCESS FOR THE PREPARATION OF AN AQUEOUS DISPERSION OF LIPID VESICLES

FIELD OF THE INVENTION

The present invention relates to a process for the preparation of aqueous dispersions of lipid vesicles and to the compositions based on the dispersions thus obtained.

The lipid vesicles of these dispersions have a lamellar structure comprising at least one sheet formed by a lipid double layer which defines an enclosed space; they encapsulate an aqueous phase advantageously comprising water-soluble active substances, for example pharmaceuticals or cosmetics, which are thus protected from the conditions on the outside. These vesicles can be produced from ionic lipids or nonionic lipids: the term "vesicle" used in the present application encompasses the two types of structure.

BACKGROUND OF THE INVENTION

French Patent Application FR-A-2,399,242 discloses a process for the preparation of liposomes in aqueous suspension, according to which a first aqueous phase, which may contain active substances, is dispersed in a solvent which is non-miscible or slightly miscible with water, in the presence of a lipid of the formula XY, where X is a hydrophilic group and Y is a lipophilic group, which makes it possible to obtain a continuous solvent phase of "liposome precursors" which consists of microscopic globules of aqueous phase whose envelope is a film of the substance XY; these "vesicle precursors" are emulsified in an aqueous medium in the presence of excess lipid XY or another lipid ZW, where Z is a hydrophilic group and W is a lipophilic group, the abovementioned solvent being removed before or after said emulsification. However, this process requires the use of sound or ultrasound waves for the dispersion of the first step, a technique which is poorly suited to productions on an industrial scale.

French Patent FR-B-2,418,023 discloses a process for the preparation of lipid, oligolamellar, synthetic capsules which are suitable to enclose a biologically active material (or materials), according to which a mixture of an organic phase which contains, in a solvent, a compound capable of forming capsule walls, with an aqueous phase which contains the biologically active material to be encapsulated is prepared, the ratio of the organic phase to the aqueous phase being such that it is suitable for providing an emulsion of the water-in-oil (W/O) type; a homogeneous emulsion of this type is formed; the organic solvent of the emulsion is evaporated until a mixture is obtained having a gel character; and this mixture is converted into a suspension of synthetic, oligolamellar capsules enclosing the biologically active material by dispersing it in an aqueous medium. However, in this process, the concentration of the lipids in the organic phase has to remain relatively low: the range indicated is 0.05 to 5% by weight, which does not make it possible to obtain in a simple manner compositions having a high concentration of vesicles. Furthermore, the emulsification is preferably achieved by ultrasound and thus hardly applicable on an industrial scale.

Japanese Patent Application 87/273,386 (published under the number 1,117,824) describes a process for the preparation of vesicles in which lipids are dissolved in an organic solvent, water is added, the solvent is removed to form a hydrated phase and this hydrated phase is dispersed in an aqueous phase to form vesicles. This process requires a treatment of the dispersion obtained in order to reduce the size of the vesicles and their size distribution, this treatment being carried out either by means of ultrasound or a homogenizer. The disadvantage of ultrasound has already been discussed; homogenization has the disadvantage, apart from the fact that it increases the temperature of the dispersion, which may be damaging to heat-sensitive encapsulated active substances, that it releases metallic particles into the medium, which may be damaging to encapsulated active substances which are sensitive to traces of metals.

French Patent Application FR-A-2,561,101 describes a process for the preparation of liposomes which consists in forming an emulsion of the W/O type by dispersing a first aqueous phase in an organic solvent which is immiscible with water in the presence of molecules comprising a lipophilic fraction and a hydrophilic fraction, then removing the major portion of the organic solvent from this W/O emulsion by a mild method, to give a concentrated W/O emulsion, and gradually adding to this emulsion with stirring a second aqueous phase which contains molecules comprising a lipophilic fraction and a hydrophilic fraction, the residual organic solvent being removed simultaneously by evaporation. In this case, the lipid concentration in the organic phase is also low: in this respect, the range given is 0.5 to 5% by weight. Moreover, the removal of the organic solvent in the second step is predominantly carried out by decanting, which requires a lot of time and is therefore detrimental to industrial application of this process.

Finally, European Patent Application EP-A-349,429 discloses a process for the preparation of dispersible colloidal systems of amphiphilic lipids in the form of sub-micron oligolamellar liposomes, whose wall is composed of these lipids and, optionally, a substance A, and whose core is composed of water or an aqueous solution optionally containing a substance B. According to this process, a liquid phase substantially composed of a solution of lipids (and, optionally, of the substance A) in a solvent which may contain the substance B in solution is prepared; a second liquid phase substantially composed of water or an aqueous solution of the substance B is prepared; the first phase is added to the second phase with moderate stirring such that virtually immediately a colloidal suspension of vesicles is obtained; if desired, all or a portion of the solvent and the water is removed so that a colloidal suspension of the required vesicle concentration is obtained. In practice, the solvents used are water-miscible solvents. The lipid concentration in the solvent given ranges from 0.1 to 10% by weight, which is very limited.

SUMMARY OF THE INVENTION

The present invention aims at proposing a process for the preparation of aqueous suspensions of lipid spherules which are well suited to industrial applications. This object is achieved according to the invention by using a water-immiscible solvent for dissolving the lipids which are to form the vesicle sheets and by dispersing this solvent phase in which the lipids are dissolved, in an aqueous phase to give an oil-in-water emulsion (O/W), stirring being employed in order to effect this dispersion. The process according to the invention has the advantage that it can be carried out at low temperature, since it is not necessary to melt the lipids which are dissolved in the solvent phase, which makes it in particular possible to encapsulate heat-sensitive active substances in the vesicles; it also makes it possible to employ a concentrated organic phase. However, the greatest and completely unexpected and inexplicable advantage is that it always leads directly to a vesicle phase of very high quality, i.e. to vesicles of low dispersity and high degrees of encapsulation, which makes a subsequent homogenization step unnecessary and thus avoids all the abovementioned disadvantages of such a step.

Furthermore, the process according to the invention is faster than the conventional process which consists in bringing the lipids into contact with the aqueous phase to be encapsulated in the vesicles, gently stirring to form a lamellar phase, adding a liquid dispersant, then stirring vigorously; indeed, the hydration step for forming the lamellar phase, which has always been a fairly long step, is omitted.

DETAILED DESCRIPTION OF THE INVENTION

Figure 1:
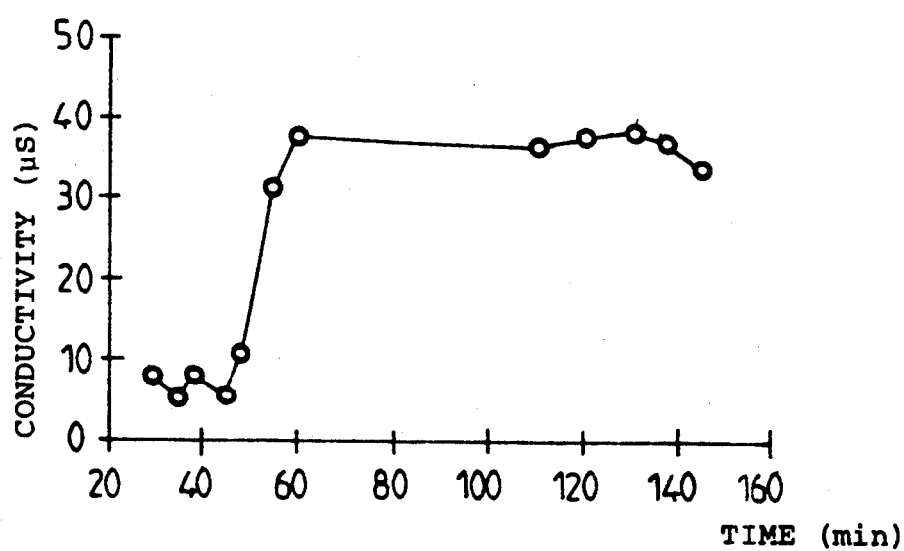
FIG. 1 is a graph of the change in conductivity of a dispersion in accordance with the invention as a function of time.

The present invention therefore first relates to a process for the preparation of an aqueous dispersion of lamellar lipid vesicles, each of which is composed of at least one spheroidal lipid sheet which encapsulates an aqueous liquid, in which:

(a) in a first step, at least one lipid is dissolved in at least one organic solvent,
(b) in a second step, the organic phase obtained in the first step is added to an aqueous phase,
(c) in a third step, the mixture from the second step is dispersed with stirring, and
(d) in a fourth step, the solvent(s) is (are) evaporated at the same time as a portion of the water, characterized in that the organic solvent(s) from step (a) is (are) immiscible with water; in that the respective amounts of the two phases from step (b) are such that the dispersion subsequently obtained is a dispersion of the oil-in-water type (O/W); and in that steps (c) and (d) are carried out with vigorous stirring, the continuous phase of the dispersion always remaining the aqueous phase.

In this process, should it become necessary, the dispersion is concentrated in a fifth step.

In step (a), all water-immiscible solvents which have a boiling point below 50° C. at a pressure between $1.5 \times 10^4$ and $10^5$ Pa and solubilize the lipids used for forming the vesicles can advantageously be used. Solvents which can be used according to the invention are dichloromethane, chloroform, ethyl acetate, butyl acetate, ethyl formate, hexane, cyclohexane, toluene, petroleum ether, and mixtures of at least two of these with one another.

Thus, in step (a) an organic phase can be prepared in which the lipid(s) is (are) present in an amount of about 5 to 50% by weight, preferably about 10 to 20% by weight, of said organic phase. This high lipid concentration is a very interesting characteristic feature of the process according to the invention.

Furthermore, step (a) of the process according to the invention is advantageously carried out at a temperature of about 35° C. to about 55° C., preferably at a temperature in the vicinity of 35° C.

The lipid(s) can be selected from nonionic amphiphilic lipids, ionic amphiphilic lipids, and mixtures of nonionic and ionic lipids.

The nonionic amphiphilic lipids are in particular selected from:

(1) linear or branched polyglycerol ethers of the formula:

in which:

—$C_3H_5(OH)O$ is represented by the following structures in a mixture or separately:

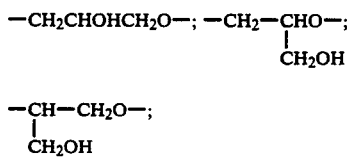

$\bar{n}$ is an average statistic value between 2 and 6;
R represents:
(a) a linear or branched, saturated or unsaturated, aliphatic chain containing 12 to 30 carbon atoms; or hydrocarbon radicals of lanolin alcohols;
(b) an $R^1CO$ radical where $R^1$ is a linear or branched aliphatic $C_{11}$–$C_{17}$ radical
(c) an $R^2$–$(OC_2H_3(R^3))$– radical where:
$R^2$ can take the meaning (a) or (b) given for R;
$OC_2H_3(R^3)$— is represented by the following structures in a mixture or separately:

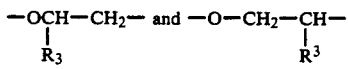

where $R^3$ takes the meaning (a) given for R;
(2) linear or branched polyglycerol ethers comprising two fatty chains;
(3) polyethoxylated fatty alcohols and polyethoxylated sterols and phytosterols;
(4) polyol ethers;
(5) ethoxylated or non-ethoxylated polyol esters;
(6) glycolipids of natural or synthetic origin;
(7) hydroxyamides having the formula:

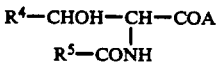

in which:
$R^4$ denotes a $C_7$–$C_{21}$-alkyl or alkenyl radical;
$R^5$ denotes a saturated or unsaturated $C_7$–$C_{31}$ hydrocarbon radical;
COA denotes a grouping selected from the following two groupings:

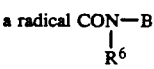

where
B is a radical derived from mono- or polyhydroxylated primary or secondary amines; and
$R^4$ denotes a hydrogen atom or a methyl, ethyl or hydroxyethyl radical; and a —COOZ radical where Z represents a $C_3$-$C_7$ polyol radical.

The ionic amphiphilic lipids are in particular selected from:
- natural phospholipids, such as egg or soya lecithin and sphingomyelin;
- synthetic phospholipids, such as dipalmitoylphosphatidyl choline or hydrogenated lecithin; and
- anionic compounds.

The evaporation of the solvent in step (d) can advantageously be carried out at atmospheric pressure, while the optional concentration of the dispersion at the end of the process is effected by entrainment of any residual solvent and of a portion of the water under reduced pressure.

The lipids can be combined with at least one additive selected from:
- long-chain alcohols and diols;
- sterols, for example cholesterol;
- long-chain amines and quaternary ammonium derivatives thereof;
- dihydroxyalkylamines; polyethoxylated fatty amines; esters of long-chain amino alcohols; and salts and quaternary ammonium derivatives thereof;
- phosphoric esters of fatty alcohols, for example dicetyl hydrogen phosphate or its sodium salt;
- alkyl sulphates, for example sodium cetyl sulphate; and
- certain polymers, such as polypeptides and proteins.

According to another specific characteristic feature of the invention, the weight ratio of the organic phase to the aqueous phase used in step (b) is between about 0.1 and about 0.6, leading to an O/W emulsion.

Furthermore, it goes without saying that at least one water-soluble active substance can be introduced into the aqueous phase and/or at least one lipid-soluble active substance into the organic phase. Thus, water-soluble active substances can be encapsulated in the aqueous phase which is encapsulated in the vesicles and lipid-soluble active substances in the vesicle sheets.

Moreover, it is important in the process according to the invention that the mixing of the organic phase containing the lipids with the aqueous phase is carried out with vigorous stirring. The stirring in steps (c) and (d) can be carried out in particular by means of rotating stirrers whose circumferential velocity is greater than 10 m/s at the free end of these devices and whose angular velocity is greater than 1000 rpm.

The preferred velocities are 40 m/s at 5000 rpm, respectively.

According to the invention, it is possible to control the vesicle size by varying the stirrer velocity during the mixing of the phases. This size can be controlled in particular between 0.2 and 0.3 μm.

The present invention likewise relates to the compositions based on the aqueous dispersions of lipid vesicles, such as are obtained by the process just described.

To provide a better understanding of the purpose of the invention, an embodiment is now described by way of a solely illustrative and non-limiting example.

EXAMPLE 1

Preparation of an aqueous dispersion of vesicles from nonionic lipids

A lipid phase formulated as follows is used (in % by weight):

Nonionic amphiphilic lipid of the formula:

in which:
R is a hexadecyl radical;
—$C_3H_5(OH)O$ represents:

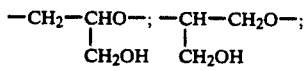

| | |
|---|---|
| n is equal to 3 | 47.5 |
| cholesterol | 47.5 |
| dicetyl phosphate | 5 |

Lipid vesicles encapsulating an aqueous phase are prepared from the following formulation (% by weight):

| | |
|---|---|
| Lipid phase defined above | 8.7 |
| Dichloromethane | 34.8 |
| (Glucose | 2 |
| (Glycerol | 2.2 |
| Aqueous phase(Water | 52.3 |
| (Preservative | In sufficient quantity |

The lipid phase is dissolved in dichloromethane at a temperature of 35° C.; the organic phase thus obtained is then added to the aqueous phase, and the mixture is dispersed over a period of 10 minutes with stirring at 5000 rpm by means of a turbine giving a circumferential velocity at the end of the blades of 40 m/s in a vessel of 50 $dm^3$ effective volume and about 40 cm in height containing 20 kg of mixture.

The dichloromethane is distilled off at about 40° C. at atmospheric pressure over a period of 55 minutes, while maintaining the same level of stirring.

The residual dichloromethane and a portion of the water are then entrained at about 40° C. over a period of 145 minutes by continuing the distillation under a reduced pressure of $4 \times 10^3$ pascals.

This gives a dispersion of vesicles having a lipid phase concentration by weight of 23.1%. It is found that the degree of encapsulation of vesicles at the end of the operation is 2.4 μl/mg with a volume fraction of 79% (the volume fraction is the ratio of the volume occupied by the vesicles to the total volume of the dispersion) and an average diameter of 200 nm. By way of comparison, it must be noted that the current processes lead to vesicle sizes of greater than 1000 nm. To obtain a finer particle size, it is necessary to use conventional homogenizers and at an equivalent lipid concentration several runs are then necessary to obtain vesicles of about 220 nm and in this case the degree of encapsulation does not exceed 2 μl/mg for volume fractions below 70%.

The changes in the dispersion during the course of this process have been monitored; the results are listed in Table 1; the time t=0 corresponds to the start of the distillation.

The change in conductivity of the dispersion during the course of the process was measured by means of a galvanometer connected to an electrode comprising two platinum wires at a distance of 0.5 cm to which a potential difference of 4 volts was applied.

The results are shown in FIG. 1 of the attached drawing: the time in minutes is plotted on the abscissa and the conductivity in μSiemens on the ordinate. It can be stated that the conductivity remains between 10 and 40 μSiemens: such a small variation is incompatible with a phase inversion; the nature of the continuous medium of the dispersion (aqueous phase) therefore does not change during the removal of the solvent.

TABLE 1

| Time (min) | $H_2O$ content (%) | $CH_2Cl_2$ content (%) | Glucose conc. (mol/l) | Lipid phase conc. (%) | Volume fraction (%) ** | Degree of encapsul. (μl/mg) | Average diam. (nm) * | Poly-dispersity |
|---|---|---|---|---|---|---|---|---|
| 30 | — | 25.7 | — | — | — | — | — | — |
| 35 | 72.2 | 20.9 | 0.126 | 4.6 | 35.8 | — | — | — |
| 38 | 72.9 | 17.5 | 0.179 | 6.5 | 55.1 | — | — | — |
| 45 | 76.8 | 11.1 | 0.207 | 8.1 | 67.9 | — | — | — |
| 48 | 81.4 | 7.4 | 0.181 | 7.5 | 62.8 | — | 347 | 0.64 |
| 55 | 79.4 | 2.7 | 0.296 | 12.0 | 74.3 | — | 229 | 0.26 |
| 60 | 79.4 | .0 | 0.341 | 13.9 | 76.7 | 4.5 | 219 | 0.20 |
| 110 | 78.5 | " | 0.360 | 14.5 | 76.0 | 4.3 | 218 | 0.19 |
| 120 | 76.3 | " | 0.408 | 15.9 | — | — | — | — |
| 130 | 72.8 | " | 0.491 | 18.3 | — | — | — | — |
| 137 | 69.8 | " | 0.568 | 20.3 | — | — | — | — |
| 145 | 65.6 | " | 0.689 | 23.1 | 79.2 | 2.4 | 221 | 0.19 |

*The particle size distribution of the dispersion was studied by means of the counter "COULTER N6" after dilution with 0.3M glucose and 0.02% of $NaN_3$
**Total volume fraction of the dispersed phase (vesicles + organic phase) (after almost all the dichloromethane has been removed, the overall volume fraction is virtually equal to the volume fraction of the vesicles)

EXAMPLE 2

Preparation of an aqueous dispersion of vesicles from nonionic lipids

A lipid phase formulated as follows is used:

$$C_{12}H_{25}[OC_2H_3(R)]\!-\!O\!-\![C_3H_5(OH)\!-\!O]_{\bar{n}}H$$

where —$OC_2H_3(R)$— is composed of a mixture of the radicals:

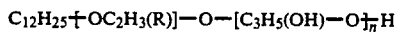

where —$C_3H_5(OH)$—O— is composed of a mixture of the radicals:

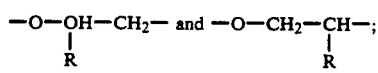

where $\bar{n}$ 1 is 6

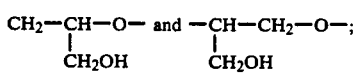

| | |
|---|---|
| and where R is a mixture of the radicals $C_{14}H_{28}$ and $C_{16}H_{33}$ | 380 g |
| cholesterol | 380 g |
| all-trans retinoic acid | 10 g |
| DL α-tocopherol | 10 g |

In a cylindrical tank of 50 dm³ effective volume and about 40 cm in height, the lipid phase is dissolved in 4000 g of dichloromethane at a temperature of 35° C.; the organic phase thus obtained is then added to 13,855 g of water, and the mixture is dispersed for 10 minutes with stirring at 5000 rpm by means of a turbine giving a circumferential velocity at the end of the blades of 40 m/s.

The dichloromethane is distilled off at about 40° C. at atmospheric pressure over a period of about 55 minutes, while maintaining the same level of stirring.

The residual dichloromethane and a portion of the water are then entrained at about 40° C. over a period of 145 minutes by continuing the distillation under a reduced pressure of $4 \times 10^3$ pascals.

This gives a vesicle dispersion having a lipid phase concentration by weight of 8%, an average vesicle diameter of 240 nm and a polydispersity index of 0.27.

EXAMPLE 3

Preparation of an aqueous vesicle dispersion from ionic lipids

A lipid phase formulated as follows is prepared:

| | |
|---|---|
| Hydrogenated lecithin based on 30/35% of hydrogenated phosphatidylcholine and sold by "NIKKO" under the name "LECINOL S 10" | 480 g |
| Polyethoxylated phytosterol (with 5 moles of ethylene oxide) sold by "NIKKO" under the name "GENEROL 122 EY 5" | 320 g |
| Mixture of methylene chloride and chloroform in a weight ratio of 81.5 to 18.5 | 3200 g |

An aqueous phase formulated as follows is prepared:

| | |
|---|---|
| Water | 13,800 g |
| Disodium salt of ethylenediaminotetraacetic acid | 10 g |

The lipid phas is dissolved in the mixture of solvents at a temperature of 35° C. to give an organic phase.

The organic phase is added to the aqueous phase in a cylindrical tank of 50 dm³ effective volume having a height of 40 cm, and the mixture is dispersed for 10 minutes with stirring at 5000 rpm by means of a turbine giving a circumferential velocity at the end of the blades of 40 m/s.

The mixture of solvents is distilled off at about 40° C. at atmospheric pressure over a period of 55 minutes, while maintaining the same level of stirring.

The residual mixture of solvents and a portion of the water are then entrained at about 40° C. over a period of 145 minutes by continuing the distillation under a reduced pressure of $4 \times 10^3$ pascals.

This gives a vesicle dispersion having a lipid phase concentration by weight of 8.1%, an average vesicle diameter of 204 nm and a polydispersity index of 0.3.

We claim:

1. A process for the preparation of an aqueous dispersion of lamellar lipid vesicles, each of which is composed of at least one spheroidal lipid sheet which encapsulates an aqueous liquid, said process comprising:
(a) in a first step, dissolving at least one lipid in at least one solvent consisting of a water immiscible organic solvent to produce an organic phase,
(b) in a second step, adding the organic phase obtained in said first step to an aqueous phase to obtain a mixture thereof, the weight ratio of said organic phase to said aqueous phase ranging from about 0.1 to about 0.6 whereby the respective amounts of the two phases are such that the dispersion subsequently obtained is an oil-in-water dispersion,
(c) in a third step, dispersing the said mixture from said second step with stirring, and
(d) in a fourth step, evaporating with stirring said water immiscible organic solvent concurrent with a portion of water,
said stirring in steps (c) and (d) being carried out by means of rotating stirrers whose circumferential velocity is greater than 10 m/s at the free end of said stirrers and whose angular velocity is greater than 1000 rpm.

2. The process of claim 1 where in step (a) said water immiscible organic solvent has a boiling point below 50° C. at a pressure ranging from $1.5 \times 10^4$ to $10^5$ pascals.

3. The process of claim 2 wherein said water immiscible organic solvent is selected from the group consisting of dichloromethane, chloroform, ethyl acetate, butyl acetate, ethyl formate, hexane, cyclohexane, toluene, petroleum ether and mixtures thereof.

4. The process of claim 1 where in step (a) said lipid is present in said organic phase in an amount of about 5 to 50 percent by weight of said organic phase.

5. The process of claim 1 wherein step (a) is carried out at a temperature between about 35° C. and 55° C.

6. The process of claim 1 wherein said lipid is selected from a nonionic amphiphilic lipid, an ionic amphiphilic lipid and a mixture of a nonionic lipid and an ionic lipid.

7. The process of claim 6 wherein said nonionic lipid is selected from the group consisting of
(1) a linear or branched polyglycol ether having the formula $ROC_3H_5(OH)O_nH$ wherein
—$C_3H_5(OH)O$ represents the following structures, separately or in a mixture:

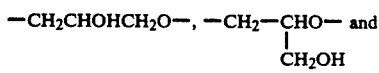

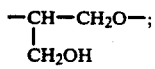

$\overline{n}$ has a statistical average value between 1 and 6; and R represents
(a) a linear or branched, saturated or unsaturated, aliphatic chain containing 12 to 30 carbon atoms, or a hydrocarbon radical of a lanolin alcohol;
(b) R'CO wherein R' is a linear or branched $C_{11}$–$C_{17}$ aliphatic radical;
(c) $R^2$—(-$OC_2H_3(R^3)$-)— wherein $R^2$ has the meaning given above in (a) or (b) for R;

$OC_2H_3(R^3)$ represents the following structures, separately or in a mixture:

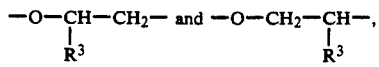

wherein $R^3$ has the meaning given above in (a) for R;
(2) a linear or branched polyglycerol ether having two fatty chains;
(3) a polyethoxylated fatty alcohol, a polyethoxylated sterol or a phytosterol;
(4) a polyol ether;
(5) an ethoxylated or non-ethoxylated polyol ether;
(6) a natural or synthetic glycolipid; and
(7) a hydroxyamide having the formula:

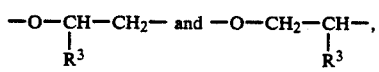

wherein
$R^4$ represents a $C_7$–$C_{21}$ alkyl or alkenyl radical;
$R^5$ represents a saturated or unsaturated $C_7$–$C_{31}$ hydrocarbon radical;
COA represents a group selected from the group consisting of

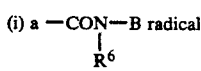

wherein
B is a radical derived from a mono- or polyhydroxylated primary or secondary amine; and
$R^6$ represents hydrogen, methyl, ethyl or hydroxyethyl, and
(ii) a —COOZ radical, wherein Z represents a $C_3$–$C_7$ polyol radical.

8. The process of claim 6 wherein said ionic amphiphilic lipid is selected from the group consisting of a natural phospholipid, a synthetic phospholipid and a anionic compound.

9. The process of claim 1 wherein said lipid is combined with at least one additive selected from the group consisting of a long chain alcohol; a long chain diol; a sterol; a long-chain amine or quaternary ammonium derivative thereof; a dihydroxy alkylamine; a polyethoxylated fatty amine; an ester of a long chain amino alcohol or a salt or quaternary ammonium derivative thereof; a phosphoric ester of a fatty alcohol; an alkyl sulphate; a polypeptide and a protein.

10. The process of claim 1 which includes (i) introducing at least one water soluble active substance into said aqueous phase, or (ii) introducing at least one lipid soluble active substance into said organic phase or (iii) both steps (i) and (ii).

11. The process of claim 1 wherein the vesicle size is controlled between 0.2 and 0.3 μm by varying stirrer velocity.

12. The process of claim 1 which includes subsequent to step (d) concentrating the said dispersion.

13. The process of claim 12 wherein concentrating said dispersion comprises entraining any residual water immiscible organic solvent and a portion of water under reduced pressure.

* * * * *